United States Patent [19]
Reid

[11] Patent Number: 5,904,145
[45] Date of Patent: May 18, 1999

[54] METHOD AND MEANS FOR TREATING LIMB SWELLING DISORDERS AND THE LIKE

[76] Inventor: Tony R. Reid, 2032 E. Grand Ave., Des Moines, Iowa 50317

[21] Appl. No.: 08/748,235

[22] Filed: Nov. 12, 1996

[51] Int. Cl.$^6$ .................................................. A61B 15/00
[52] U.S. Cl. ........................... 128/898; 606/201; 606/202
[58] Field of Search ..................................... 128/898, 892, 128/869, 877, 878, 882; 606/201, 202, 203

[56] References Cited

U.S. PATENT DOCUMENTS

| | | |
|---|---|---|
| 1,629,108 | 5/1927 | Lake . |
| 3,856,008 | 12/1974 | Fowler et al. ........................... 128/165 |
| 3,888,242 | 6/1975 | Harris et al. . |
| 4,150,442 | 4/1979 | Boone . |
| 4,186,738 | 2/1980 | Schleicher et al. . |
| 4,338,923 | 7/1982 | Gelfer et al. ........................... 128/24 R |
| 4,369,588 | 1/1983 | Berguer . |
| 4,383,342 | 5/1983 | Forster . |
| 4,421,110 | 12/1983 | DeLisle et al. . |
| 4,573,456 | 3/1986 | Spann . |
| 4,971,041 | 11/1990 | Millikan et al. . |
| 5,007,411 | 4/1991 | Dye . |
| 5,179,941 | 1/1993 | Siemssen et al. . |
| 5,218,954 | 6/1993 | van Bemmelen . |
| 5,383,842 | 1/1995 | Bertini . |
| 5,383,894 | 1/1995 | Dye . |
| 5,591,200 | 1/1997 | Cone et al. ............................ 606/201 |

Primary Examiner—Mickey Yu
Assistant Examiner—Dinh X. Nguyen
Attorney, Agent, or Firm—Zarley,McKee,Thomte, Voorhees & Sease

[57] ABSTRACT

An apparatus for treating lymphedema in the limb of a patient as an outer sleeve configured to encircle the limb of the patient. A plurality of straps are secured in a lateral configuration on the sleeve to tighten the sleeve about the limb of the patient. Detachable markers are located on each of the straps adjacent a reference point on the straps to permit the straps to be tightened, loosened and then retightened to the same positions. The method for treating edema in the limb of a patient at a multiplicity of spaced apart locations comprises encircling the limb of a patient with an elongated sleeve having an elongated open seam and a plurality of spaced apart laterally extending releasable enclosable tightening straps. Strap are closed to secure the sleeve to the patient's limb. One of the straps is released, and a partially air-inflated pneumatic bladder is inserted through the seam underneath the released strap to position the bladder adjacent the patient's limb and the interior of the sleeve. The released strap is then closed and tightened against the bladder to cause a predetermined increase of pressure to be achieved within the bladder. The tightened strap that extends over the bladder is then released and the bladder is removed from the sleeve. The strap that extended over the bladder is then tightened to the same tightened position that existed prior to the bladder being removed. The foregoing steps are then sequentially repeated in regard to the remaining straps.

8 Claims, 4 Drawing Sheets

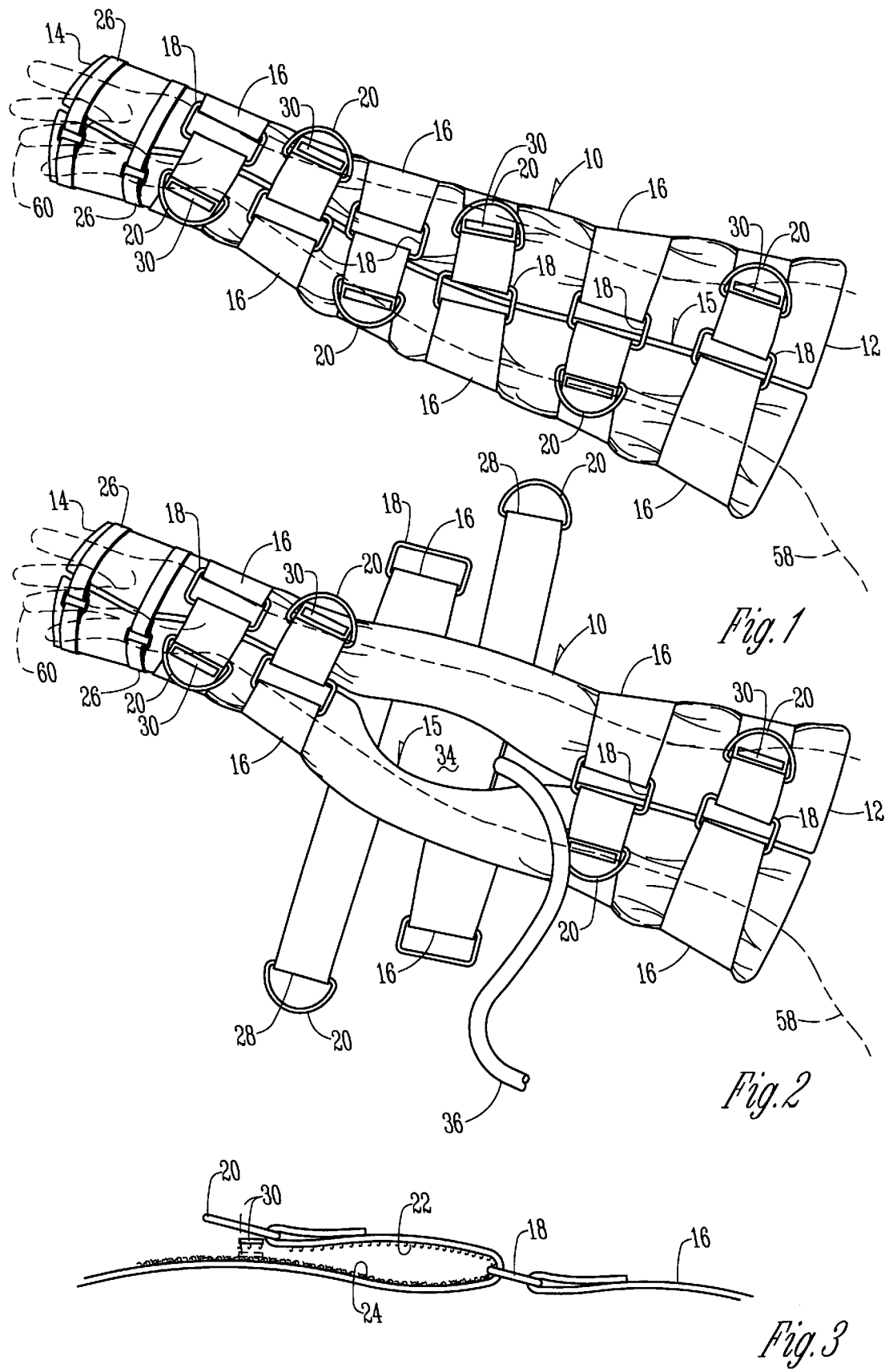

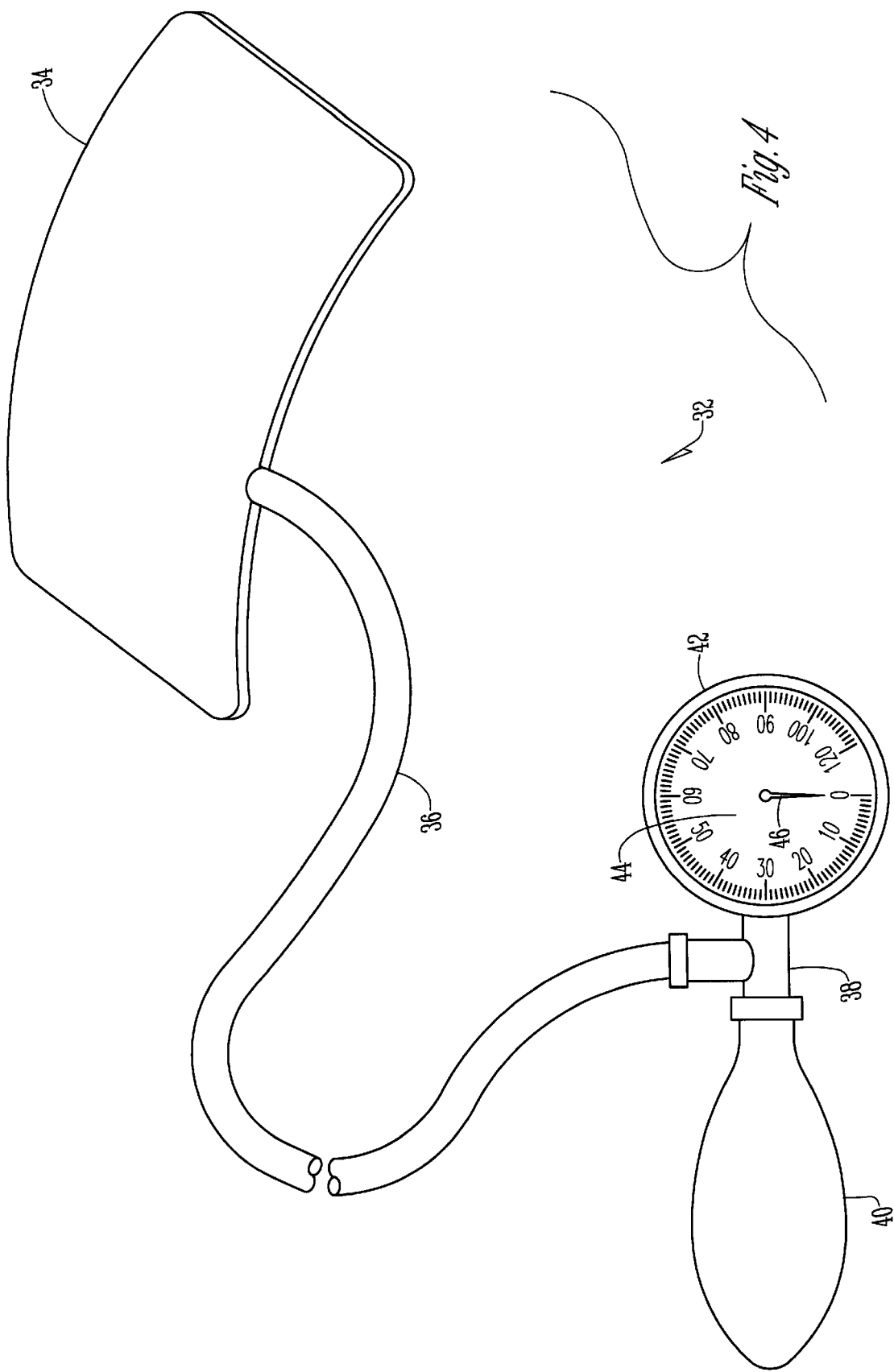

METHOD AND MEANS FOR TREATING LIMB SWELLING DISORDERS AND THE LIKE

BACKGROUND OF THE INVENTION

Lymphedema is the accumulation of excessive lymph fluid and swelling of subcutaneous tissues due to the obstruction or destruction of lymph vessels. In breast cancer patients, lymphedema occurs in the arm and results in painful swelling. Excessive fluid accumulation, referred to as edema, can also arise in the arms, legs and, trunk from a variety of other causes, including infection, radiation therapy, and other conditions which result in damage to or destruction of portions of the lymphatic and/or venous system.

Sleeve devices have been previously used to apply pressure at various locations along the length of an arm, for example, to relieve swelling due to lymphedema and other causes. Such sleeves have a plurality of laterally extending strap elements which can be tightened to exert pressure points or lines against the skin to permit the release and flow back of fluid to the remaining healthy lymph nodes. Such a device and method of use are disclosed in co-pending application U.S. application Ser. No. 08/390,866 now abandoned. While such devices are effective, they incur some difficulty in use because they provide no way to measure the hardness or softness of the arm, and they provide no way of determining how much pressure should be or is applied to the limb being treated. One of the problems in this area of medicine is to measure how soft or hard the arm is. Is there a lot of fluid that is easily displaced, or is the tissue hard and fibrotic? Understanding this helps us guide therapy. Different treatments are used if the tissue is soft or hard. The soft, fluid filled edema is called pitting edema. In pitting edema, application of pressure with a finger, for example, will cause the fluid to move away from the area where the pressure is applied and will leave an impression of the finger, or a pit. After the pressure is removed, the impression of the finger will remain for some time. In other conditions there is no pitting, the tissue is hard and fibrotic and no pit is left in the skin after the application of pressure with a finger.

It is therefore a principal object of this invention to provide a method of determining the hardness or softness of the limb being treated.

A further object of the invention is to provide a method of determining the amount of pressure to be applied to the limb being treated.

A still further object of this invention is to provide a sleeve apparatus that will permit predetermined pressure to be applied to spaced apart areas of the limb being treated.

These and other objects will be apparent to those skilled in the art.

SUMMARY OF THE INVENTION

A limb sleeve is provided which has an elongated open seam with a plurality of laterally extending pressure straps extending therearound. The sleeve has a girth that will encircle the limb being treated. Such a sleeve is disclosed in said co-pending U.S. application Ser. No. 08/390,866. The pressure straps have removable indicia patches thereon to permit the operator to tighten each strap sufficiently to exert a predetermined amount of pressure on the arm as permitted by the method of this invention.

The method of this invention is employed after the attending physician decides the magnitude of the pressure to be applied to limb based upon several factors including the limb tissue of a specific patient, the degree of swelling, and possibly other factors. Typically, the applied pressure is within the range of 15–45 mm of mercury. The physician will then take a device very similar to a conventional blood pressure measuring device which includes an elongated flexible hollow inflatable bladder, an elongated flexible tube having one end in communication with the interior of the bladder, and an opposite end secured to an air pump bladder and a pressure recording device having a visible pressure indicia dial.

The bladder is placed within the space between a pair of stationary platens, and the bladder is precharged with a quantity of air to measure, for example, 10 mm of mercury. The bladder is then removed from the platens, whereupon the pressure indicia dial will return to a zero reading.

The limb of the patient is then inserted in the pressure sleeve, and the pressure straps are randomly affixed. Then, one by one, the pressure straps are released, and the bladder is inserted through the partially opened seam under the released strap. The released strap is then closed and tightened against the bladder to compress the bladder sufficiently to the desired pressure against the limb. Thus, if it was desired to exert pressure in the amount of 30 mm of mercury against the arm, the strap would be tightened until the needle on the pressure recording device moved to the numeral "30". A detachable indicia marker would then be attached to the strap adjacent the tightening buckle to let the operator know the degree to which the strap should be tightened to achieve 30 mm of pressure against the arm. With the indicia marker in place, the strap is loosened, the bladder is removed from the sleeve, and the strap is then again tightened to its previous position indicated by the indicia marker. These steps are then repeated for each pressure strap on the sleeve.

The knowledge of the hardness or softness of the patient's limb is helpful in guiding the therapy of the patient, either in conjunction with the foregoing process or in other therapeutic procedures. To determine the hardness or softness of the limb tissues, the bladder is filled with a fixed, small amount of air and placed on the arm and then compressed. If the pressure of the bladder causes fluid to move, the bladder will expand, and the pressure in the bladder will fall. The rate and degree of pressure change in the bladder is determined by the gauge connected to the bladder. As in the case of the finger causing pitting, the bladder will cause pitting in the edematous arm. The pressure in the bladder is then monitored at intervals to assess tissue changes.

BRIEF DESCRIPTION OF THE DRAWINGS

FIG. 1 is a perspective view of the therapeutic sleeve of this invention;

FIG. 2 is a view similar to that of FIG. 1 wherein the sleeve of FIG. 1 is partially opened to practice the method of this invention;

FIG. 3 is an enlarged scale side view of the connecting elements at the ends of the pressure or tightening straps;

FIG. 4 is an enlarged scale view of the air pressure apparatus used in the method of this invention;

DESCRIPTION OF THE PREFERRED EMBODIMENT

Figure 5:
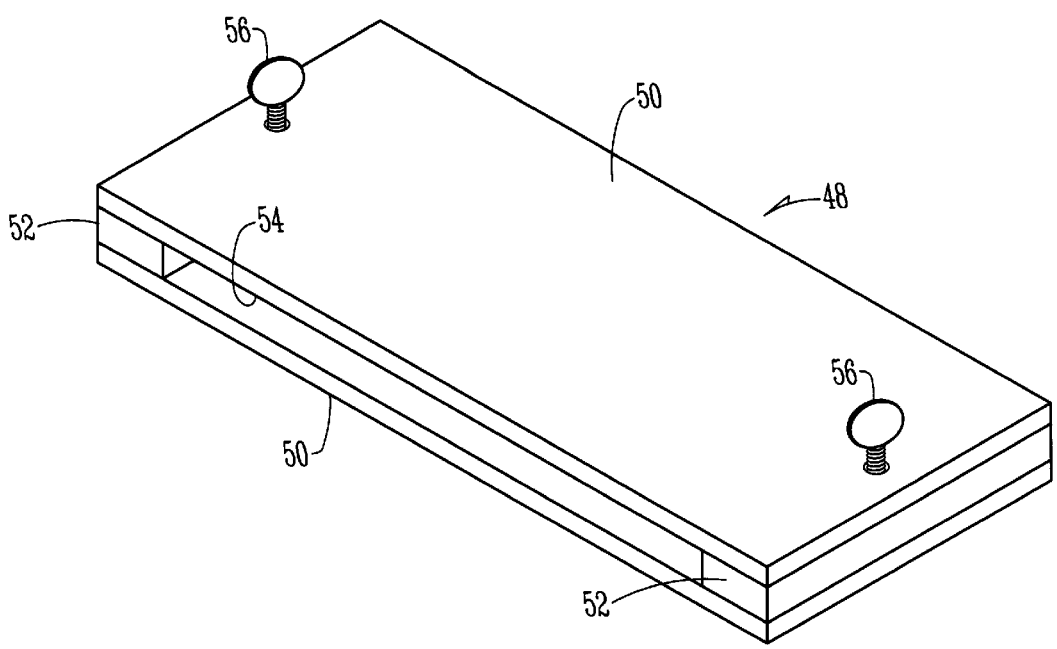
FIG. 5 is an enlarged scale perspective view of the pre-inflation guide.
Figure 6:
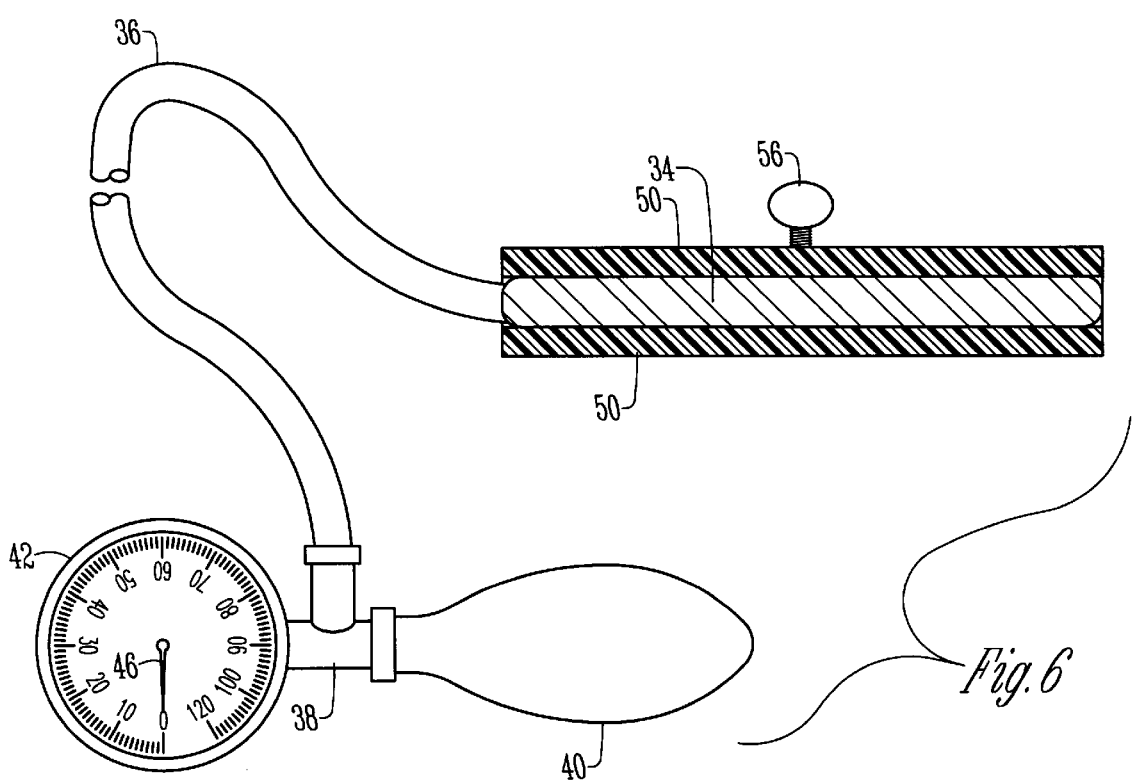
FIG. 6 is a lateral sectional view through the pre-inflation guide of FIG. 5 with the bladder of the pressure apparatus of FIG. 4 inserted therein.

The term "limb" as used herein will refer to the arm or the leg of a patient as well as any other portion of the patient's body that is to be treated.

FIG. 1 shows the therapeutic sleeve 10 as used in this invention. With the exception of one element of structure to be described hereafter, the sleeve 10 is the same as the therapeutic sleeve disclosed in U.S. patent application Ser. No. 08/390,866 referred to herebefore. The sleeve 10 has all of the structure disclosed in said application, and the description of the sleeve as set forth in the prior application is incorporated by reference herein.

Sleeve 10 has an enlarged end portion 12 and a hand portion 14 of a smaller magnitude. Pressure or tightening straps 16 are affixed to the outer surface of the sleeve 10 in any convenient manner such as by stitching or the like (not shown). An elongated open seam 15 extends longitudinally down sleeve 10 and is created by the adjacent side edges of the sleeve. A square open buckle 18 is secured in a convenient manner to one end of each of the straps 16. Similarly, a grasping buckle 20 is similarly secured to the other end of each of the straps 16. As best shown in FIG. 3, a plurality of fastening hooks 22 are secured to a portion of the surface of the ends of strap 16 adjacent buckles 20 and are adapted to be detachably secured to conventional loops 24 which are also secured along the length of strap 16 adjacent to hooks 22. (FIG. 3). The numeral 28 designates a strap end adjacent buckle 20 which serves as a reference line or point for detachable marker element 30. Marker element 30 is rectangular in shape and has a plurality of hooks 22 thereon adapted to be detachably secured to the loops 24 as will be described hereafter. With reference to FIG. 4, a pressure apparatus 32 which is very similar to a conventional blood pressure testing device, comprises a hollow flexible pneumatic bladder 34. Tube 36 has one of its ends in communication with the interior of bladder 34, with the other end secured to T-connector 38. A conventional pneumatic pump 40 is also mounted on connector 38 opposite a conventional pressure gauge 42. Gauge 42 has an indicia face 44 and a conventional indicia pointer 46 centrally located thereon. The pressure gauge 42, through indicia face 44 and indicia pointer 46 reflects the amount of air pressure within the bladder 34 when in a compressed state.

With reference to FIG. 5, a pre-inflation guide 48 is comprised of a pair of parallel rectangular rigid platens 50 which are mounted on an end blocks 42. End blocks 42 create an open space 54 between the platens 50. The upper platen 50 is detachably secured to the end blocks by conventional set screws 56.

The numerals 58 and 60 in FIGS. 1 and 2 designate the patient's arm and hand, respectively.

Figure 7:
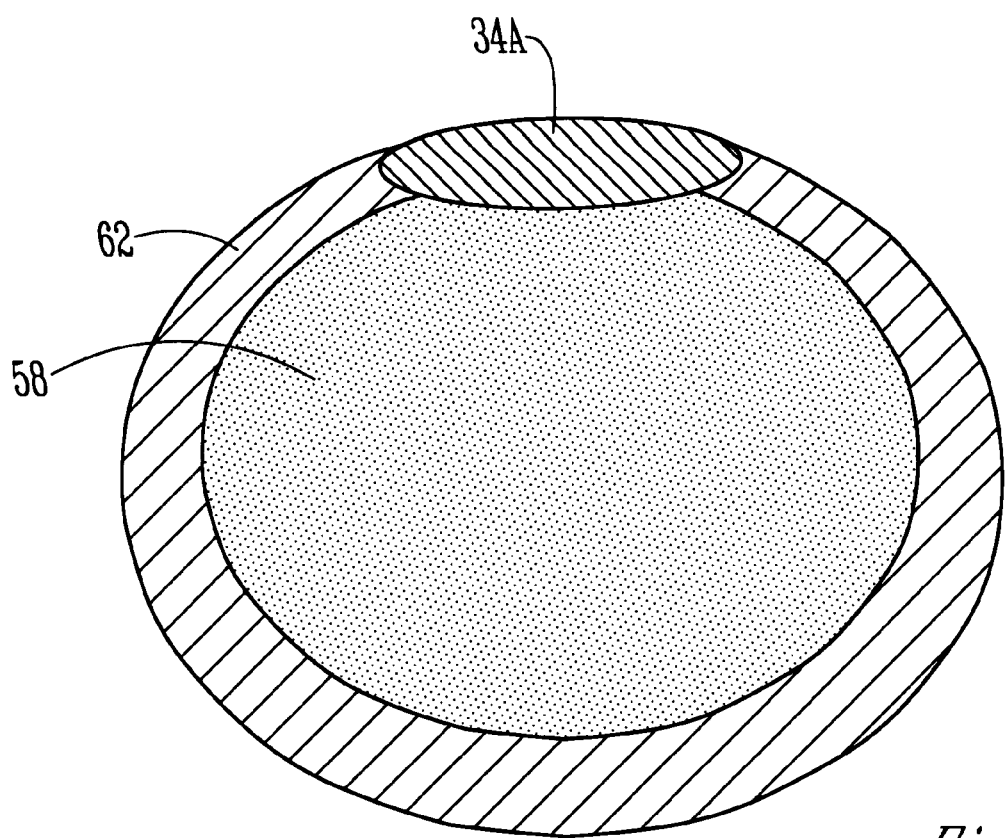
FIG. 7 is an enlarged sectional view through the arm of a patient showing the apparatus used to determine the softness or the hardness of the tissues of the patient's arm.

With reference to FIG. 7, a bladder 34A similar to the bladder 34 and the related structure in FIG. 4 is placed upon the patient's arm 58 and is secured thereto by a conventional band 62 or the like. The interconnection of the band 62 to the bladder 34A is not critical and could assume any one of a number of different interconnections.

The softness or hardness of the patient's arm is determined by utilizing the structure of FIG. 7 wherein the band 62 is utilized to place the bladder 34A in direct contact with the outer surface of the patient's arm or limb. The bladder is inflated with a fixed and small amount of air. If the pressure of the bladder causes fluid in the arm to move, the bladder will expand, and the pressure in the bladder will fall. This will be determined by a gauge such as the gauge 42 and the related structure shown in FIG. 4. The rate and degree of pressure change in the bladder is determined by the gauge 42, and the pressure in the bladder is monitored at intervals to assess tissue changes.

In operation, the sleeve 10 is placed around the limb of the patient as best illustrated in FIG. 1 and described in the prior application Ser. No. 08/390,866. This is accomplished by extending the straps 16 across the seam 15 and threading the buckles 20 through the buckles 18 and doubling the end of the straps 16 adjacent the buckle 18 back upon itself and securing the hooks 22 to the loops 24 as best shown in FIG. 3. After the physician has determined the amount of pressure to be imposed at spaced locations on the patient's limb, as discussed above, the bladder 34 is placed in space 54 between the platens 50 by removing the upper platen 50 through the use of set screws 56, placing the bladder within the opening 54, and then replacing the upper platen 50, again by utilizing the set screws 56. Approximately 10 mms of mercury pressure is injected into the bladder 34.

Upon the removal of the bladder 34 from the assembly 48, at least one of the straps 16 is released, and the partially inflated bladder 34 is inserted within seam 15 to assume a position between the arm of the patient and the interior surface of the sleeve 10 (FIG. 2). The released strap 16 is thereupon again closed to compress the bladder 34. If the physician has decided, for example, that 30 mms of mercury pressure are to be applied to the patient's arm, the release strap 16 is tightened until the needle 46 on gauge 42 registers with the number 34 on the indicia face 44.

The marker element 30 is then placed on strap 16 adjacent the strap end 28 to indicate the degree of tightness that the release strap 16 must be tightened to achieve the 30 mms of pressure. When the marker 30 is placed in position, the release strap 16 is thereupon released; the bladder 34 is removed from within the sleeve 10, and the released strap 16 is thereupon retightened on the arm of the patient so that the marker 30 is adjacent the strap end 28. The marker 30 is therefore useful in enabling the operator to tighten the release strap 16 back to the same position as existed when the bladder 34 was within the sleeve 10.

This process is thereupon repeated for each of the straps 16. This process will then assure that a predetermined amount of pressure is applied at all pressure locations on the patient's arm. If for any reason the physician determines that a different amount of pressure should be exerted at the location of some of the straps 16, this result can be easily accommodated by merely tightening a release strap to a different value as reflected on the gauge 42.

It is therefore seen that this invention will achieve at least all of its stated objectives.

What is claimed is:

1. A method for treating edema in the limb of a patient at a multiplicity of spaced apart locations, comprising, encircling the limb of the patient with an elongated sleeve having an elongated open seam and a plurality spaced apart laterally extending releasable and closable tightening straps, closing said straps to secure said sleeve to the patient's limb, releasing one of said straps, inserting a partially air-inflated pneumatic bladder through said seam underneath said released strap to position said bladder adjacent the patient's limb and the interior of said sleeve, said bladder being partially inflated to a predetermined pressure by placing said bladder between fixed spaced platens and injecting air into said bladder, closing and tightening said released strap against said bladder to cause a predetermined increased pressure to be achieved within said bladder, releasing the tightened strap that extends over said bladder, removing said bladder from said sleeve, and tightening said strap that extended over said bladder to the same tightened position that existed prior to said bladder being removed, and repeating said aforementioned steps with regard to other of said tightening straps.

2. The method of claim 1 wherein a detachable marker element is placed on said released strap to denote the position of said released strap at the initial tightened position thereof over said bladder so that said released strap can be returned to the same initial tightened position after said bladder is removed from said sleeve.

3. The method of claim 1 wherein an air pressure gauge outside said sleeve is attached to said bladder so that the air pressure within said bladder can be determined when said released strap is extending over said bladder in a tightened condition.

4. The method of claim 1 wherein said released strap extending over said bladder is tightened around the patient's limb to achieve a predetermined amount of pressure against the limb of the patient.

5. The method of claim 3 wherein said released strap extending over said bladder is tightened around the patient's limb to achieve a predetermined amount of pressure against the limb of the patient.

6. The method of claim 2 wherein said marker is positioned adjacent a reference point on said released strap.

7. The method of claim 1 wherein said bladder is partially inflated to a predetermined pressure.

8. The method of claim 1 wherein the air pressure within said bladder is measured when said bladder is positioned between said platens and air is being injected therein.

* * * * *